United States Patent
Parrish

(10) Patent No.: US 11,266,721 B1
(45) Date of Patent: Mar. 8, 2022

(54) METHODS OF TREATING OR PREVENTING AGE RELATED DISORDERS

(71) Applicant: BioViva USA Inc., BainBridge, WA (US)

(72) Inventor: Elizabeth Louise Parrish, Bainbridge, WA (US)

(73) Assignee: BIOVIVA USA INC., Bainbridge, WA (US)

(*) Notice: Subject to any disclaimer, the term of this patent is extended or adjusted under 35 U.S.C. 154(b) by 0 days.

(21) Appl. No.: 15/369,783

(22) Filed: Dec. 5, 2016

Related U.S. Application Data

(60) Provisional application No. 62/325,158, filed on Apr. 20, 2016.

(51) Int. Cl.
*A61K 38/45* (2006.01)
*A61K 38/17* (2006.01)
*A61P 39/00* (2006.01)

(52) U.S. Cl.
CPC .......... *A61K 38/45* (2013.01); *A61K 38/1709* (2013.01); *A61P 39/00* (2018.01); *C12Y 207/07049* (2013.01)

(58) Field of Classification Search
CPC ..... A61K 38/45; A61K 38/1709; A61P 39/00; C12Y 207/07049
See application file for complete search history.

(56) References Cited

PUBLICATIONS

Bernardes de Jesus et al.; Telomerase gene therapy in adult and old mice delays aging and increases longevity without increasing cancer; EMBO Molecular Medicine, vol. 4, No. 8, Aug. 1, 2012, pp. 691-704 (Year: 2012).*
Manix et al.; Creutzfeldt-Jakob disease: updated diagnostic criteria, treatment algorithm, and the utility of brain biopsy; Neurosurgical Focus, vol. 39, E2, pp. 1-11, Nov. 2015 (Year: 2015).*
Aoyagi et al.; Cancer cachexia, mechanism and treatment; World J Gastrointest Oncol Apr. 15, 2015; 7(4): 17-29 (Year: 2015).*
Vickers; A vaccine against Alzheimer's disease: developments to date. Drugs Aging 2002; 19(7):487-94 (Year: 2002).*
Callaway; Telomerase reverses ageing process; Nature News; published Nov. 28, 2010, pp. 1-3 (Year: 2010).*
De Magalhaes et al.; Telomeres and Telomerase: A Modern Fountain of Youth?; Rejuvenation Research; vol. 7, No. 2, 2004, pp. 126-133 (Year: 2004).*

* cited by examiner

*Primary Examiner* — Antonio Galisteo Gonzalez
(74) *Attorney, Agent, or Firm* — Workman Nydegger

(57) ABSTRACT

This invention relates to the treatment of age-related disorders with a combination of the hTERT gene and the Follistatin gene in a delivery system such as in an adeno-associated viral vector. The Follistatin gene is expected to promote the division of stem cells that will regenerate the organism and the hTERT will prevent their depletion.

15 Claims, No Drawings

Specification includes a Sequence Listing.

SEQUENCE LISTING

```
<160> NUMBER OF SEQ ID NOS: 2

<210> SEQ ID NO 1
<211> LENGTH: 1035
<212> TYPE: DNA
<213> ORGANISM: Homo sapiens

<400> SEQUENCE: 1
atggtccgcg cgaggcacca gccgggtggg ctttgcctcc tgctgctgct gctctgccag      60
ttcatggagg accgcagtgc ccaggctggg aactgctggc tccgtcaagc gaagaacggc     120
cgctgccagg tcctgtacaa gaccgaactg agcaaggagg agtgctgcag caccggccgg     180
ctgagcacct cgtggaccga ggaggacgtg aatgacaaca cactcttcaa gtggatgatt     240
ttcaacgggg gcgcccccaa ctgcatcccc tgtaaagaaa cgtgtgagaa cgtggactgt     300
ggacctggga aaaatgccg aatgaacaag aagaacaaac cccgctgcgt ctgcgccccg      360
gattgttcca acatcacctg gaagggtcca gtctgcgggc tggatgggaa aacctaccgc     420
aatgaatgtg cactcctaaa ggcaagatgt aaagagcagc cagaactgga agtccagtac     480
caaggcagat gtaaaaagac ttgtcgggat gttttctgtc caggcagctc cacatgtgtg     540
gtggaccaga ccaataatgc ctactgtgtg acctgtaatc ggatttgccc agagcctgct     600
tcctctgagc aatatctctg tgggaatgat ggagtcacct actccagtgc ctgccacctg     660
```

```
agaaaggcta cctgcctgct gggcagatct attggattag cctatgaggg aaagtgtatc    720
aaagcaaagt cctgtgaaga tatccagtgc actggtggga aaaaatgttt atgggatttc    780
aaggttggga gaggccggtg ttccctctgt gatgagctgt gccctgacag taagtcggat    840
accttgttct gtgccagtga caatgccact tatgccagcg agtgtgccat gaaggaagct    900
gcctgctcct caggtgtgct actggaagta aagcactccg gatcttgcaa ctccatttcg    960
gaagacaccg aggaagagga ggaagatgaa gaccaggact acagctttcc tatatcttct   1020
attctagagt ggtaa                                                    1035

<210> SEQ ID NO 2
<211> LENGTH: 817
<212> TYPE: RNA
<213> ORGANISM: Homo sapiens

<400> SEQUENCE: 2
aggccgcgcg aggcaccagc cgggggggcgc cccgcgcgcg ccgccagcag gaggaccgca     60
ggcccaggcg ggaacgcggc ccgcaagcga agaacggccg cgccaggccg acaagaccga    120
acgagcaagg aggaggcgca gcaccggccg gcgagcaccc gggaccgagg aggacggaag    180
acaacacacc caagggagac aacggggggcg cccccaacgc accccgaaag aaacgggaga    240
acgggacggg accgggaaaa aagccgaaga acaagaagaa caaaccccgc gcgcgcgccc    300
cggagccaac acaccggaag ggccagcgcg ggcggaggga aaaccaccgc aagaaggcac    360
ccaaaggcaa gagaaagagc agccagaacg gaagccagac caaggcagag aaaaagacgc    420
gggagcgcca ggcagcccac aggggggacc agaccaaaag ccacgggacc gaacggagcc    480
cagagccgcc ccgagcaaac cggggaagag gagcaccacc caggccgcca ccgagaaagg    540
caccgccgcg ggcagacagg aagccagagg gaaaggacaa agcaaagccg gaagaaccag    600
gcacggggga aaaagagggg acaaggggga gaggccgggc cccggagagc ggcccgacag    660
aagcggauau ccgcggccag gacaagccac agccagcgag ggccagaagg aagcgccgcc    720
ccaggggcac ggaagaaagc acccggacgc aacccacgga agacaccgag gaagaggagg    780
aagagaagac caggacacag cccaaccaca gagggaa                            817
```

METHODS OF TREATING OR PREVENTING AGE RELATED DISORDERS

CROSS-REFERENCE TO RELATED APPLICATION

CONTINUITY CLAIMED FOR PROVISIONAL APPLICATION No. 62/325,158, Apr. 20, 2016

STATEMENT REGARDING FEDERALLY SPONSORED RESEARCH OR DEVELOPMENT

Applicable

NAMES OF PARTIES TO A JOINT RESEARCH AGREEMENT

Not Applicable

REFERENCE TO SEQUENCE LISTING, A TABLE, OR A COMPUTER PROGRAM LISTING COMPACT DISK APPENDIX

Not Applicable

BACKGROUND

This inventor has discovered a method to bring the 1999 teachings of Michael West of Geron to their culmination of regeneration not limited to individual cells in vitro but their regeneration within the human tissue they compose. The administration of the Follistatin gene is expected to promote the division of stem cells that will regenerate the organism and the hTERT will prevent their depletion. Both of these genes are available from sources well known to those of ordinary skill in the art. The regeneration of a human being will ultimately prove the concept and culminate decades of work.

Tert Gene

Telomerase is a ribonucleoprotein that catalyzes the addition of telomeric repeats to the ends of telomeres. Telomeres are long stretches of repeated sequences that cap the ends of chromosomes. In humans, telomeres are typically 7-10 kb in length and comprise multiple repeats. Telomerase is not expressed in most adult cells, and telomere length decreases with successive rounds of replication. Telomerase acts as reverse transcriptase in the elongation of telomeres, which prevent the loss of telomeres due to the end replication problems. Without telomerase the telomeres are shortened at each cell division which leads to senescence, apoptosis and cell death caused by chromosome instability. Telomerase is inactive in somatic cells but active in 90% of cancer cells, where telomerase is reactivated. Although telomerase activation may be dangerous, because it can mimic the cancer development process, telomerase enhancing agents may be theoretically applicable as anti-aging agents and clinically useful in certain medical conditions. In contrast, telomerase inhibitors may be useful to fight cancer. Cancer and aging are closely inter-related: Interventions that protect against cancer can lead to premature aging while immortalization of cells is required in the formation of malignant cancer cells. Despite the theoretical risk of activation of carcinogenesis, activation of telomerase may lead to reduced rate of aging.

Lack of telomerase activity and/or expression and short telomeres may cause dyskeratosis congenita, aplastic anemia, increase of death due to cardiovascular diseases, strokes or infections, hypertension or chronic stress. It was shown that transduction of telomerase in telomerase knockout mice prevented damage in the liver. In addition to the role of telomerase in telomere length maintenance, accumulating data suggest that the telomerase reverse transcriptase (TERT) protein has additional physiological functions, i.e. protecting cells and mice from various damages in a mechanism (yet unclear) that does not involve telomere elongation.

Decades of work with telomerase and telomeres prove that such technology can be used successfully to regenerate aging cells and tissue to rejuvenate the human body and restore it to a level similar to youthful function. Since shortly before the turn of the century, research into the potential of interventions in telomerase in regenerative medicine. In 1999, scientists at Geron demonstrated that through the use of telomerase activation the aged cell could not only reset its Hayflick limit but could revert its gene expression to an earlier point in its life cycle. Shelton, Dawne N et al., Current Biology 9,17 (1999): 939-945. After 2000, evidence has continued to mount that the restoration of telomeres in fact convey stability of gene expression, youthful function and a level of protection against cancer. The stable gene expression of youth may likely account for the rarity of cancer and resistance to disease and dysfunction enjoyed during youth.

Age reversal has since been shown in fibroblasts and keratinocytes of the elderly that with their telomere length reset to that of younger skin, will express the phenotype of younger skin. Telomerase activation can reverse the age of a cell to a youthful state not only in appearance but also in terms of function and gene expression. Funk, Walter D et al., Experimental Cell Research 258.2 (2000): 270-278. Similar results have been demonstrated with human vascular cells, Matsushita, Hidetsugu et al., Circulation Research 89.9 (2001): 793-798, elderly osteoclasts (bone cells). Yudoh, Kazuo et al., Journal of Bone and Mineral Research 16.8 (2001): 1453-1464. The conclusion that telomerase activation extends the telomeres and leads to a return of youthfulness in all cell types. In the early $21^{st}$ century, Ronald DePhinho published studies on the inhibitory effect of telomerase on telomere loss in the aging cell. Sahin, Ergun, and Ronald A DePinho, Nature 464.7288 (2010): 520-528, Jaskelioff, Mariela et al., Nature 469.7328 (2011): 102-106, Sahin, Ergun, and Ronald A DePinho. Nature reviews Molecular cell biology 13.6 (2012): 397-404, Sahin, Ergiin et al., Nature 470.7334 (2011): 359-365.

Unfortunate and unfounded concerns that telomerase might promote neoplastic change chilled the development of its potential during the 1990's were not shown as unfounded until 2011 in the explanations published by Wright and Shay in 2011. Shay, Jerry W, and Wright, Woodring E., Seminars In Cancer Biology, 31 Dec. 2011: 349-353; Harley, Calvin B., Oncogene 21.4 (2002): 494-502; and Blasco. Maria A., et al., Cell 91.1 (1997): 25-34; de Jesus, Bruno Bernardes, and Blasco, Maria A., Trends in Genetics 29.9 (2013): 513-520. Experiments showed that immune function in particular can show significant improvement with the use of weak telomerase activators as part of a health regimen. Harley, Calvin B et al., Rejuvenation research 14.1(2011): 45-56. In 2012, Mario Blasco demonstrated that cellular age could be reversed by the delivery of telomerase via an adeno associated viral (AAV) vector, de Jesus, Bruno Bernardes et al., EMBO Molecular Medicine 4.8 (2012): 691-704, and created a model for demonstrations of the regenerative potential of telomerase and the resetting of cellular telomeres, Bar, Christian et al. Nature Communications 5 (2014), and further reviews some of the multiple potential methodologies of the administration of telomerase as an anti-aging therapy. de Jesus, Bruno Bernardes, and Maria A Blasco., Current Opinion In Cell Biology 24.6 (2012): 739-743.

Comparison of gene expression in youthful, elderly, and TERT treated cells demonstrates that in eighty-four percent of the initially up-regulated and eighty-six percent of the down regulated genes showed at least a 1.2-fold reversion to youthful profiles. Lackner, Daniel H et al. Aging Cell 13.5 (2014): 946-950. While expression was not in all cases completely restored, only a few genes failed to show any reversion. Importantly, in cells that had reserves of telomeres, the activation of TERT had no effect on gene expression showing that there is a natural optimum point of telomere extension. This paves the way for development of further telomerase therapeutics and may lead to whole body organ rejuvenation and restoration of youthful gene expression. Mobilization of stem cells in their niches is a key process in organ homeostasis and continued function. Maria Blasco has demonstrated that telomerase activity is linked to mobilization of stem cells, specifically in the dermis, Flores, Ignacio, Maria L Cayuela, and Maria A Blasco., Science 309.5738 (2005): 1253-1256, though likely a universal mechanism. Conversely, the loss of telomeres inhibited stem cell mobilization from the niche leading to impairment of hair growth and skin cell proliferation, but TERT expression promotes cell mobilization independent of telomere length. This demonstrates an additional role of telomerase in the cell not only in its ability to regulate genes and limit replication but also its ability to mobilize dormant stem cells to regenerate cells and tissue, an important regenerative implication. Flores, Ignacio, and Maria A Blasco. FEBS letters 584.17 (2010): 3826-3830.

The ability of TERT to regenerate via stem cell activation and WNT and MYC pathways is a key component to this rejuvenation, Choi, Jinkuk et al., PLoS Genet 4.1 (2008): e10, in addition to the changes in cell gene expression controlled by the telomeres. This regenerative potential was again recently demonstrated in the treatment of myocardial infarction, Bar, Christian et al., Nature Communications 5 (2014), and last year the rejuvenation of telomeres in skin and muscle cells was again demonstrated with use of modified RNA to activate the telomerase gene, Ramunas, John et al. The FASEB Journal 29.5 (2015): 1930-193, and the aged cell returned to youthful gene expression and function. Fibroblasts thus treated divided forty times in an additional to their functional lifespan without observed negative effects. Eventually, cells resumed aging showing that the effect was transient but that cellular age is elastic.

The genes of this invention can be delivered in one of the modalities known to one of ordinary skill in the art such as a viral, protein, ligand, plasmid, or liposomal delivery system. In one embodiment, the adeno-associated viral (AAV) vector platform is used to insert genes to treat a disorder and are modified for the enhanced delivery to neural tissue. The virus delivers the genes of interest to the subjects cells. In recent years AAV gene therapies have been tested in humans with great success and no evidence of adverse effects. There are numerous clinical trials currently being conducted with AAV gene therapy for many diseases.

The Epigenetic/Telomere Theory of Aging

The telomere theory of aging can be put in one sentence: Cells divide, telomeres shorten, gene expression changes, cellular repair and recycling slow down, errors slowly accumulate, and cells fail. Originally considered to be simple counters of cell division, telomeres as well as protecting the chromosome from damage also affect the gene expression of all the genes on that chromosome through a mechanism known as the telomere position effect (TPE). Wright and Shay and a number of other leading scientists have demonstrated how the telomeres affect this gene expression throughout life [11]. These changes in gene expression in effect reprogram the cell as the telomeres shorten and contribute to the dysfunctional changes associated with aging. This programmed change of gene expression and resulting dysfunction is different to changes in gene expression through DNA methylation and histone acetylation patterns called epigenetic drift although they share similarities. Both processes are influenced by genotype, both appear to result in stem cell dysfunction, both occur independently of tissue and finally both are linked to disease risk factors. Epigenetic drift likely constitutes a second aging "clock" within the cell and should be the focus of life extension therapies in conjunction with telomere restoration to potentially restore youthful cell function. Dr. Michael Fossel, one of the foremost advocates of the telomere or epigenetic theory of aging, explains that it is not the absolute length of telomeres which control aging, but the level of erosion relative from the time the egg was fertilized. As Fossel explains, "Telomere length is irrelevant, telomere loss is critical." Fossel, Michael B., M.D., Cells, Aging, and Human Disease, Oxford University Press, New York, N.Y. (2004): 36. In summary, the rate of telomere shortening appears to depend on the telomeres original length.

People starting out with the longest telomeres experience the fastest rate of telomere shortening and vice versa and explains how mice, with significantly longer telomeres compared to ours, still have shorter life spans. So it is the restoration of telomere loss to its initial length that is the goal here rather than simply extending them as much as possible. This shortening eventually causes the cell to enter senescence not because the chromosomes are not properly capped, but because the gene expression has altered to the point that the cell ceases to be functional. The question over whether some older people have enough senescent cells to explain their aged tissue is resolved by the fact that cell senescence is only part of the picture. Gene expression patterns cause the older phenotypes to be expressed and functionality to become reduced, in all of the cells of elderly. Coupled with changes in gene expression, senescent cells cause further damage as a significant number of these exhausted cells resist apoptosis, their natural death, and remain in place and send out damaging signals known as the senescence-associated secretory phenotype (SASP). They are a part of the larger picture and aside from cancer are some of the most dangerous and dysfunctional cells, being incapable of division and are in fact toxic to neighboring cells via SASP. A relatively small number of such cells create a far greater problem and the area of senolytic agents capable of removing them has been of considerable interest recently.

The objection to the epigenetic theory that the slow division of certain cell populations, neurons, cardiomyocytes and myocytes poses is overcome by the requirements of these slowly dividing cells for support from their dividing neighbors. Each neuron, for example, is surrounded by Glial cells, which do divide and whose telomeres do shorten and their support is lost in old age. Moreover, age compromises the blood supply to the brain as the cells of the arteries begin aging due to the gene expression changes caused by telomere erosion. For every non-dividing tissue type this loss of support from their neighboring dividing cells is consistent with the pathology that we observe in the non-dividing tissues as they age. In conclusion, telomeres are a primary target of interventions to promote the reversal in gene expression that will mitigate the effects of aging and revert cells to a younger healthier pattern of expression. Numerous experiments demonstrate that restoring relative telomere length rejuvenates cells and the tissue they comprise, in both animal and human cells tested. This is why after decades of testing and research it is finally time to develop this as a restorative therapy with the potential to address a myriad of age associated conditions and to potentially extend lifespan considerably.

Follistatin Gene

Growth and differentiation factor-8 (GDF-8), also known as myostatin, is a member of the transforming growth factor-beta (TGF-.beta.) superfamily of structurally related growth factors, all of which possess important physiological growth-regulatory and morphogenetic properties. GDF-8 is a negative regulator of skeletal muscle mass, and there is considerable interest in identifying factors which regulate its biological activity. For example, GDF-8 is highly expressed in the developing and adult skeletal muscle. The GDF-8 null mutation in transgenic mice is characterized by a marked hypertrophy and hyperplasia of the skeletal muscle. Similar increases in skeletal muscle mass are evident in naturally occurring mutations of GDF-8 in cattle.

Of the factors that enhance the formation of muscle and factors that inhibit muscle formation and myostatin is one of the main factors that inhibit muscle growth, but there are related proteins with similar functions. myostatin and related proteins bind to receptors on the muscle cells and signal the myocyte to stop growing. When the gene for the myostatin protein is mutated and no myostatin is made, this leads to increased muscle formation in animals (Belgian blue cows, Texel sheep and greyhounds) and humans. Thus, if it is possible to prevent myostatin from doing its job, this should enhance muscle formation. This could compensate for the loss of muscle tissue in sarcopenia, muscular dystrophy and other muscular wastage conditions and can be achieved by gene therapy for myostatin inhibition. These antibodies bind to myostatin and prevent it from reaching the gene switches and turning down the level of expression thus mitigating the loss of muscle. Follistatin is a protein that inhibits myostatin, a protein that inhibits muscle growth and thus by increasing the levels of Follistatin, the inhibitor is inhibited, which will lead to an increase in muscle mass. The Follistatin gene has been delivered to mice and monkeys using an AAV viral vector and the injections resulted in an increase in muscle mass and muscle strength, similar promising results have been demonstrated in a recent gene therapy for Becker's MD with some excellent results in some patients.

The Follistatin gene as a full-length version encodes a 344-amino acid preprotein, FS344, differing by a 27-amino acid sequence from its carboxy-shortened version of the 317-amino acid form. Prior to activation, follistatin, like myostatin, undergoes further post-translational modification to lose another 29 amino acids by removal of the signal peptide that results in polypeptides of 315 (FS315), often referred to as the long isoform and 288 (FS288), called the short isoform. Animal studies have shown that the administration of an alternatively spliced FS344 gene in adeno-associated viral (AAV) vector resulted in increases in muscle mass and strength in several species. Rodino-Klapac, L., et al, 39(3) Muscle Nerve: 283-296 (2009). In February of this year, follistatin was shown to be one of only three proteins that are reduced in amyotrophic lateral sclerosis, along with interleukin-1 alpha, and kallikrein-5, when statistically compared to age-matched controls. Lind, A L et al, 11(2) PLoS ONE: 2-17 (2016). The DNA is set forth as SEQ ID NO 3 of U.S. Pat. No. 8,895,309 to Kasper and Mendell, Nov. 25, 2014 and was submitted to the GENBANK as SEQ ID NO 3 of WO2008067480 filed contemporaneously, on Nov. 27, 2007.

DESCRIPTION OF INVENTION

This inventor has discovered a method of treating or preventing age-related disorders in a subject comprising administering to the subject a therapeutically effective amount of a human Telomerase Reverse Transcriptase (hTERT) gene in combination with a Follistatin gene. Follistatin is characterized according to its number of base pairs as Follistatin-344, Follistatin315, Follistatin288 or Follistatin303; the Follistatin-344 gene is the most preferred in this invention. Specifically, the subject may be any mammal such as an ovine (sheep), bovine (cattle), porcine (hogs or pigs), murine (rats or mice) or primate (apes, monkeys and humans) mammal; most specifically a human. The hTERT and Follistatin-344 genes are administered in a delivery method selected from the group consisting of an adeno-associated viral vector, protein, ligand, plasmid, liposomal or other applicable delivery method and may be administered in a number of intravenous, subcutaneous or intramuscular injections, most specifically that number is between 1 and 6 for both the hTERT and the Follistatin-344 gene. The hTERT gene may be administered in a dosage between 5×10E15 and 5×10E17 units and the Follistatin gene, most specifically as the Follistatin-344 gene, may be administered in a dosage between 5×10E14 units and 5×10E16 units. In a more specific embodiment, the hTERT gene may be administered in a dosage between 5×10E15 and 5×10E17 units and the Follistatin-344 gene may administered in a dosage between 5×10E14 units and 5×10E16 units. Most specifically, the hTERT gene is administered in a dosage of 5×10E17 units by intravenous injection in an adeno-associated viral vector and the Follistatin-344 gene is administered in five (5) intramuscular injections of 10×E16 units, by adeno-associated viral vector (AAV-F5344). The hTERT and Follistatin-344 genes may be administered in a nucleic acid selected from a plasmid, phage, viral particle, bacterial artificial chromosome (BAC), or yeast artificial chromosome (YAC), and the viral particle may be an adeno-associated viral (AAV) vector, a herpesvirus vector, or a baculovirus vector.

Disorders treated by this invention may be one related to age such as a wasting disorder, a metabolic disorder, or a disorder of the connective tissue. Wasting disorders effectively treated include those selected from the group of cachexia, anorexia, sarcopenia, skin atrophy, and muscle wasting disorders and metabolic disorders effectively treated include those selected from the group consisting of obesity, metabolic syndrome, syndrome X, renal disease, hyperglycemia, anorexia, and type II diabetes. Disorders of the connective tissue may be those of bone, blood or cartilage including osteoarthritis, osteoporosis, and cardiovascular disorders such as hypertension, hyperlipidemia, hypercholesterolemia, hyperhomocysteinemia, atherosclerosis, arteriosclerosis, myocardial infarction, congestive heart failure, peripheral vascular disease, pulmonary emphysema, stroke and anemia. Age-related disorders are often neurogenerative and include Alzheimer's disease, cataracts, age-related hearing loss, dementia, chronic traumatic encephalopathy (CTE), brain atrophy, amyotrophic lateral sclerosis (ALS), Parkinson's disease, Gillian-Barre syndrome, peripheral neuropathy, macular degeneration, Creutzfeldt-Jakob disease, dementia associated with trauma, frontotemporal dementia, spinal muscular atrophy, and Friedreich's ataxia, all of which may be prevented or treated by method of this invention.

The methods of the inventions may be used to increase muscle tissue growth in a subject by administering to a subject a therapeutically effective amount of a human Telomerase Reverse Transcriptase (hTERT) gene in combination with a Follistatin-344 gene, in a number of intravenous, subcutaneous or intramuscular injections between 1 and 6. Clinical studies comparing this administration to the administration of a placebo show a two at least two-fold greater than the muscle tissue growth of a corresponding subject treated with placebo. The hTERT and Follistatin-344 genes may be administered in a nucleic acid selected from a plasmid, phage, bacterial artificial chromosome (BAC), yeast artificial chromosome (YAC) or viral particle such as an adeno-associated viral (AAV) vector, a herpesvirus vector, or a baculovirus vector.

The genes may be are administered as peptides. The peptides may be administered with a nucleic acid selected from a plasmid, phage, bacterial artificial chromosome (BAC), or yeast artificial chromosome (YAC) or viral particle such as an adeno-associated viral (AAV) vector, a herpesvirus vector, or a baculovirus vector.

The composition of peptides that may be administered with a nucleic acid selected from a plasmid, phage, viral particle, bacterial artificial chromosome (BAC), or yeast artificial chromosome (YAC). It is therapeutically effective for increasing muscle tissue mass and for treating or preventing age-related disorders such as a wasting disorder such as cachexia and anorexia; a metabolic disorder such as obesity and type II diabetes; a cardiovascular disorder such as atherosclerosis, arteriosclerosis, myocardial infarction, congestive heart failure, peripheral vascular disease and stroke; a disorder of the bones and connective tissue such as osteoarthritis, osteoporosis, and fibromyalgia. The composition treats or prevents an age-related neurodegenerative disorder such as Alzheimer's disease, cataracts, age-related hearing loss, dementia, chronic traumatic encephalopathy (CTE), brain atrophy, amyotrophic lateral sclerosis (ALS), Parkinson's disease, Gillian-Barre syndrome, peripheral neuropathy, macular degeneration, Creutzfeldt-Jakob disease, dementia associated with trauma, frontotemporal dementia, spinal muscular atrophy, and Friedreich's ataxia.

Example

To explore the potential to save lives lost to the frailty kills 6% of the USA population The AAV therapy is tested in twenty subjects of sixty (60) years or older. In that group, each subject receives a 5×10E17 unit injection, intravenous injection of the hTERT gene in an adeno-associated viral vector along with five (5) intramuscular injections of 10 E16 units of the Follistatin gene in an adeno-associated viral vector at monthly intervals for twelve months. On the baseline day and every three months for twelve months, subjects are tested for metrics, MRI, CT, angiogram, grip test and other biomarkers of aging. In this study, increased muscle mass and physical robustness are observed in fifteen (15) study subjects of which eight (8) report a dramatic improvement in physical stamina. Of those five (5) who fail to show observable improvements, three report greater energy or less need for sleep and only two report no change, neither of whom complained the he or she feels "older" since the study began.

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

The invention claimed is:

1. A method of reducing osteoporosis in a mouse, the method comprising administering to the mouse a therapeutically effective amount of a human Telomerase Reverse Transcriptase (hTERT) gene in combination with a Follistatin-344 gene to reduce osteoporosis.

2. The method of claim 1, wherein said hTERT and Follistatin-344 genes are administered in a nucleic acid selected from a plasmid, phage, bacterial artificial chromosome (BAC), or yeast artificial chromosome (YAC), or viral particle.

3. The method of claim 2 wherein the nucleic acid is a viral particle selected from an adeno-associated viral (AAV) vector, a herpesvirus vector, or a baculovirus vector.

4. The method of claim 1, wherein said hTERT gene and said Follistatin-344 gene are administered in a number of intravenous, subcutaneous or intramuscular injections between 1 and 6.

5. The method of claim 4, wherein said hTERT gene is administered in a dosage between 5×10E15 and 5×10E17 units and said Follistatin-334 gene is administered in a dosage between 5×10E14 units and 5×10E16 units.

6. A method, comprising administering to a mouse a therapeutically effective amount of a human Telomerase Reverse Transcriptase (hTERT) gene in combination with a Follistatin-344 gene so as to improve type II diabetes and/or reduce osteoporosis.

7. The method of claim 6, wherein said hTERT and Follistatin-344 genes are administered in a nucleic acid selected from a plasmid, phage, bacterial artificial chromosome (BAC), or yeast artificial chromosome (YAC), or viral particle.

8. The method of claim 7 wherein the nucleic acid is a viral particle selected from an adeno-associated viral (AAV) vector, a herpesvirus vector, or a baculovirus vector.

9. The method of claim 6, wherein said h IERT gene and said Follistatin-344 gene are administered in a number of intravenous, subcutaneous or intramuscular injections between 1 and 6.

10. The method of claim 9, wherein said hTERT gene is administered in a dosage between 5×10E15 and 5×10E17 units and said Follistatin-334 gene is administered in a dosage between 5×10E14 units and 5×10E16 units.

11. A method of reducing osteoporosis and/or increasing muscle mass in a mouse, the method comprising administering to the mouse a therapeutically effective amount of a human Telomerase Reverse Transcriptase (hTERT) gene in combination with a Follistatin-344 gene to reduce osteoporosis and/or increase muscle mass.

12. The method of claim 11, wherein said hTERT and Follistatin-344 genes are administered in a nucleic acid selected from a plasmid, phage, bacterial artificial chromosome (BAC), or yeast artificial chromosome (YAC), or viral particle.

13. The method of claim 12 wherein the nucleic acid is a viral particle selected from an adeno-associated viral (AAV) vector, a herpesvirus vector, or a baculovirus vector.

14. The method of claim 11, wherein said hTERT gene and said Follistatin-344 gene are administered in a number of intravenous, subcutaneous or intramuscular injections between 1 and 6.

15. The method of claim 14, wherein said hTERT gene is administered in a dosage between $5 \times 10E15$ and $5 \times 10E17$ units and said Follistatin-334 gene is administered in a dosage between $5 \times 10E14$ units and $5 \times 10E16$ units.

* * * * *